United States Patent [19]

Luukkala

[11] 4,335,613

[45] Jun. 22, 1982

[54] APPARATUS FOR INDICATING THE FREEZING OF THE SURFACE OF AN ASPHALT ROAD, PAVED RUNWAY, OR THE LIKE

[75] Inventor: Mauri Luukkala, Espoo, Finland
[73] Assignee: Vaisala Oy, Finland
[21] Appl. No.: 193,915
[22] Filed: Oct. 6, 1980
[30] Foreign Application Priority Data Oct. 10, 1979 [FI] Finland ................................. 793148

[51] Int. Cl.³ ............................................ G01N 29/00
[52] U.S. Cl. ..................................... 73/599; 340/582
[58] Field of Search .................. 73/599, 590; 340/582

[56] References Cited
U.S. PATENT DOCUMENTS 2,789,281 4/1957 Short et al. ..................... 340/582

Primary Examiner—Anthony V. Ciarlante
Attorney, Agent, or Firm—Steinberg & Raskin

[57] ABSTRACT

A detecting transmitter device installed in operative proximity with a surface to be observed includes an ultrasonic waveguide installed in such surface. Electronic equipment electrically connected to the ultrasonic waveguide transmits ultrasonic waves to the waveguide. The ultrasonic waves proceed in the waveguide. The equipment also receives the ultrasonic waves from the waveguide. The degree of attenuation of the waves in the waveguide depend upon the difference in viscosity and other mechanical properties of water and ice, whereby the detecting transmitter device and the electronic equipment detect freezing of the surface by attenuation of the waves in the waveguide.

9 Claims, 4 Drawing Figures

APPARATUS FOR INDICATING THE FREEZING OF THE SURFACE OF AN ASPHALT ROAD, PAVED RUNWAY, OR THE LIKE

BACKGROUND OF THE INVENTION

The present invention relates to apparatus for indicating the freezing of the surface of an asphalt road, paved runway, or the like. The apparatus comprises a detecting transmitter device installed in operative proximity with the surface to be observed.

In the autumn and spring a thin layer of water spread over the surface of an asphalt road or paved runway of an airfield can unexpectedly freeze. This makes the road or runway slippery and hazardous for traffic. This phenomenon is called "the black ice problem", since it is often very difficult to tell whether the black surface of an asphalt road is frozen or is only covered by a thin layer of water. Attempts have been made to observe the formation of "black ice" by, for example, temperature detectors, which are installed under the surface of the asphalt, and conductivity gauges. These methods have not been successful due to several drawbacks. The road surface might, for example, be treated with salt, which makes the measurement of temperature and conductivity unreliable.

SUMMARY OF THE INVENTION

The principal object of the invention is to provide apparatus which reliably indicates whether or not there is an ice layer on the surface of an asphalt pavement.

An object of the invention is to provide apparatus for indicating the freezing of the surface of an asphalt road, paved runway, or the like, with efficiency, effectiveness and reliability.

Another object of the invention is to provide apparatus of simple and durable structure for reliably indicating the freezing of the surface of an asphalt road, paved runway, or the like.

In accordance with the invention, a detecting transmitter device of the apparatus comprises a wire-shaped or tape-shaped, appropriately dimensioned ultrasonic waveguide installed on the surface of the pavement being observed. The apparatus comprises electronic equipment for producing and detecting the ultrasonic waves proceeding in said waveguide. The detecting transmitter device and equipment detect freezing of the surface of the pavement by attenuation of the ultrasonic waves in the waveguide; the degree of attenuation of the ultrasonic waves depending upon the difference in viscosity and other mechanical properties of water and ice.

The operation of the apparatus of the invention is based on the use of ultrasound in a manner whereby a suitable ultrasonic pulse is transmitted into a metallic wire or tape ultrasonic waveguide. The pulse in the waveguide reflects from one wall to another. When the waveguide is spread across an asphalt road, or the like, in accordance with the invention, it is possible to conclude from the proceeding properties of the wave whether or not the surface of the road is frozen. This is based on the fact that a wave proceeding in the waveguide is affected by the mechanical properties of its surroundings in a manner whereby the attenuation of the wave varies with the viscosity of the surrounding material. The difference between the viscosity of water and ice is extremely great, and the operation of the ultrasonic apparatus of the invention is based on the detection of this difference in viscosity.

In the apparatus of the invention, magnetostrictive wire such as, for example, Ni wire, can be used as the waveguide. A suitable coil or winding is wound around the wire thereby producing an ultrasonic pulse in the wire by conducting a voltage pulse in the winding. The returning ultrasonic wave is detected by so called inverted magnetostriction, which means that a pulse proceeding in the wire produces a voltage in the winding.

In a tape-shaped waveguide, an ultrasonic pulse can most easily be produced by soldering a wire-shaped waveguide to the end of the tape. The ultrasonic pulse for the detection of the congealment of water in the immediate vicinity of the tape is then transferred from the wire to the tape by the so called mode conversion.

BRIEF DESCRIPTION OF THE DRAWINGS

For a fuller understanding of the invention, reference is had to the following description taken in connection with the accompanying drawings, in which.

DESCRIPTION OF PREFERRED EMBODIMENTS

Figure 1:
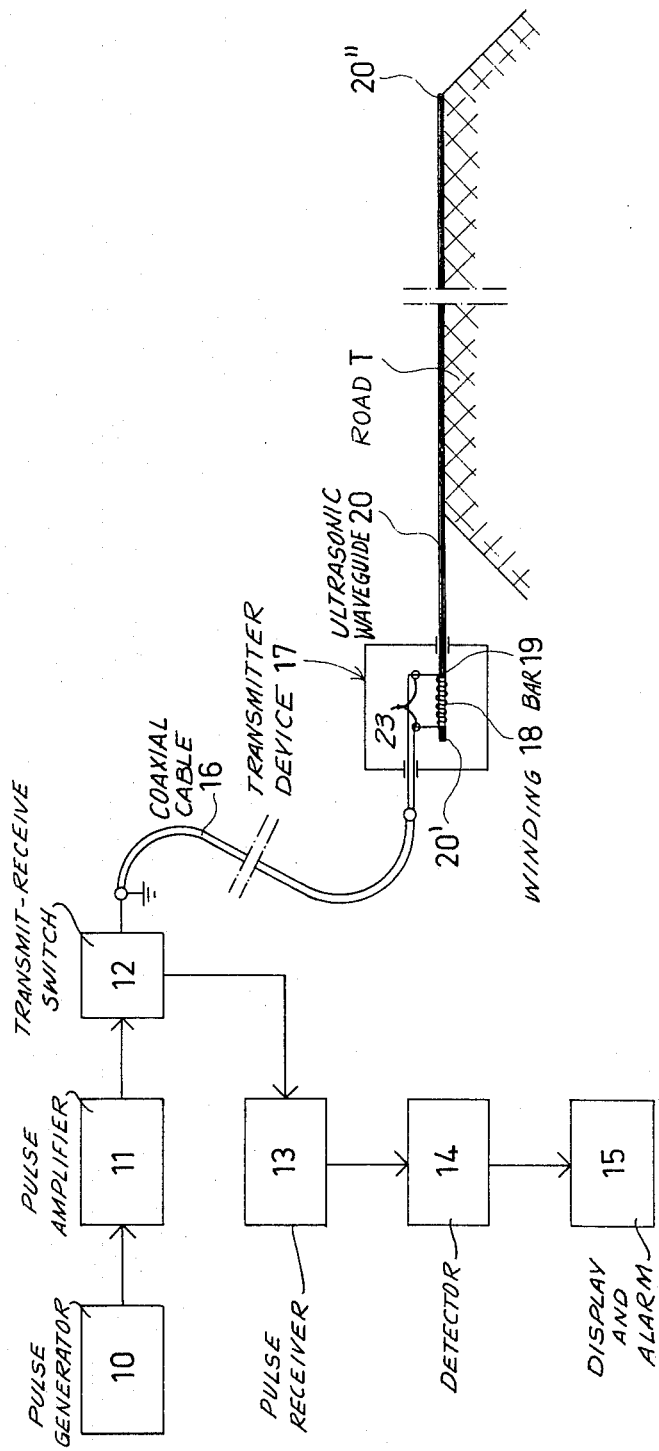
FIG. 1 is a block diagram of an embodiment of the apparatus of the invention.

As shown in FIG. 1, a pulse generator 10 produces ultrasonic pulses having a frequency f. The pulses are conducted to a pulse amplifier 11 and then to a transmit-receive switch 12 known in the art. The apparatus also comprises a pulse receiver 13, a detector 14 and a display and alarm 15. The transmit-receive switch 12 is electrically connected via a coaxial cable 16 to a transmitter device 17.

Figure 2:
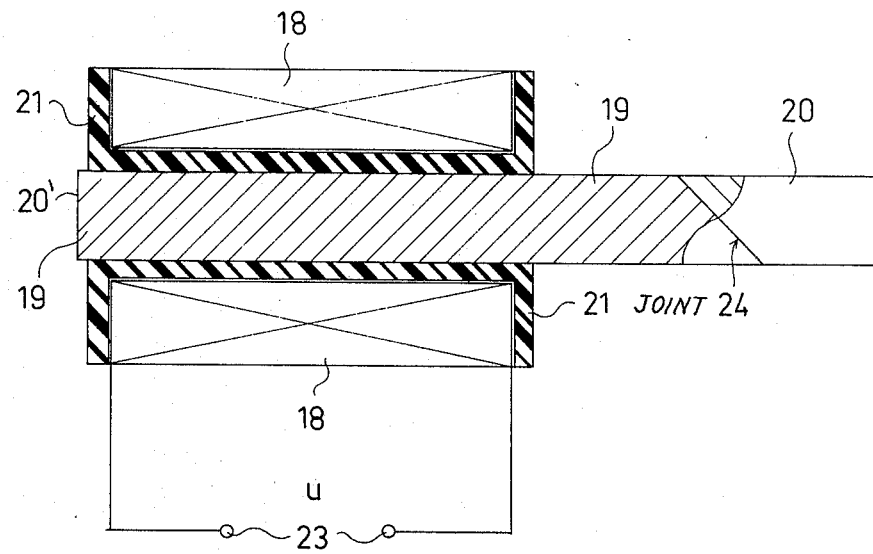
FIG. 2 is a cross-sectional view, on an enlarged scale, of an embodiment of a magnetostrictive transmitter of the invention for producing an ultrasonic wave in the tape or wire, and via which the attentuated wave is received.
Figure 4:
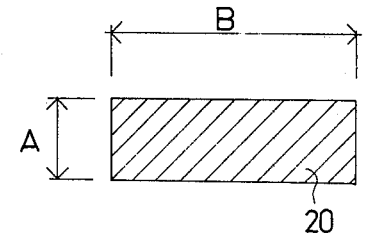
FIG. 4 is a cross-sectional view, on an enlarged scale, of an embodiment of a tape-shaped waveguide of the invention.

The transmitter device 17 includes a bar 19 of magnetostrictive material such as, for example, nickel or other suitable alloy. A coil core 21 of insulating material (FIG. 2) is wound around the bar 19 and a winding 18 wound around said core (FIG. 2). Ultrasonic voltage pulses are conducted to terminals 23 of winding 18 via the coaxial cable 16, as shown in FIG. 1. The bar 19 of magnetostrictive material is connected to an ultrasonic waveguide 20 via a suitable joint 24 (FIG. 2). The ultrasonic waveguide 20 has a wire-shaped cross-section (FIG. 3) or a tape-shaped cross-section (FIG. 4).

Figure 3:
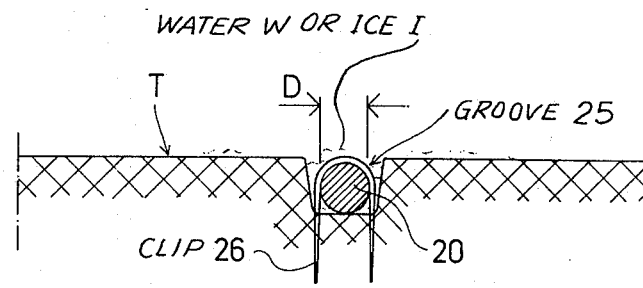
FIG. 3 is a cross-sectional schematic diagram, on an enlarged scale, illustrating how the waveguide of the invention is installed in the asphalt pavement of a road.

As shown in FIGS. 1 and 3, the waveguide 20 is installed in a groove 25 in the surface of the asphalt pavement of a road, airfield runway, or the like. The waveguide 20 is affixed to the pavement by clips 26 (FIG. 3), for example. It is not necessary to affix the waveguide 20 to the pavement via clips, or the like. Tape or wire functioning as the waveguide 20 must by no means be installed in the pavement so that a water or ice layer would be prevented from being formed between the tape or wire and the surface of the surrounding pavement.

The waveguide 20 extends over the entire width of a road T (FIGS. 1 and 3). One end 20" of the waveguide 20 is at one edge of the road and the other end 20' of said waveguide is at the end of the winding 18, as shown in FIG. 1. The wire or tape comprising the waveguide 20 is made of Ni wire, an alloy containing titanium, acid-proof steel, or some other equivalent material with a sufficiently high resistance against mechanical wear for a sufficiently long waveguide reinstallation interval.

The apparatus of the invention functions as follows. Voltage pulses of ultrasonic frequency are produced in the pulse generator 10. The switch 12 is in its "transmit" position, so that voltage pulses are conducted via the coaxial cable 16 to the winding 18. The pulses produce a magnetic field in the winding 18. Due to magnetostriction, the magnetic field produces corresponding vibrations in the bar 19. The vibrations proceed in the waveguide 20 and reflect from its walls. The attenuation of the pulse proceeding in the waveguide 20 is detected in accordance with the same principles as in echo-sounding. Due to inverted magnetostriction, the attenuated echoing pulse produces a voltage pulse in the winding 18. The voltage pulse is conducted by the coaxial cable 16 and the switch 12, which is then in its "receive" position, to the pulse receiver 13, which is connected to the display and alarm equipment 15 via the detector 14.

Water on the surface of the pavement of an asphalt road, or the like, comes into contact with the tape or wire comprising the waveguide 20. The attenuation of the pulse proceeding in the waveguide 20 depends upon whether the water on the pavement is in the form of ice I or water W (FIG. 3). This phenomenon is based on the fact that there is a considerable difference in the viscosity of water and ice.

The freezing detected by ultrasound may, by means of the aforedescribed transmitting-receiving apparatus, be indicated digitally, for example, by signifying the full digital voltage as dry or wet asphalt and as a zero-level digital signal signifying an ice layer on the asphalt. This digital signal can then be used in various signalling systems in observation stations, airports, etc.

An indication provided by the apparatus of the invention is independent of whether the pavement has been treated with salt, since it only detects freezing. A temperature detector, however, detects a temperature of 0° C., and thus does not necessarily indicate whether or not the surface is frozen. By definition, freezing always includes congealment or a sharp change of viscosity.

The frequency f of the ultrasonic waves used in the apparatus of the invention is preferably in the range $f = 100 \ldots 150$ KHz. Since the sonic speed in the metals used as waveguides is approximately 3000 meters per second, the frequency range corresponds to a wavelength in the range $\lambda = 2 \ldots 3$ cm.

The maximum dimension of the cross-section of the wire comprising the waveguide 20 is preferably less than approximately $\lambda/10$.

The diameter D of the circular cross-sectional waveguide wire 20 shown in FIG. 3 is approximately 2 mm, for example. In the tape-shaped waveguide shown in FIG. 4, the smaller dimension $A \approx 2$ mm and the larger dimension $B \approx 6$ mm. The cross-sectional dimensions of the waveguide 20 may vary within the range depending on the wavelength, for example. However, the diameter D of the wire is preferably smaller than $\lambda/10$ and the larger dimension B of the tape is preferably smaller than $\lambda/10$ for avoiding dispersion. When necessary, higher or lower ultrasonic frequencies than those in the aforementioned frequency range $f = 100 \ldots 150$ kHz may be used.

The apparatus of the invention may either be based on the measurement of the attenuation of a proceeding pulse or on the measurement of a stationary wave.

In comparing the apparatus of the invention with echo sounding, it may simply be stated that an echo is received from the waveguide 20 of the invention, when the surface surrounding the waveguide is dry or covered by water, and no echo is received when the surface surrounding the waveguide is frozen.

The invention is by no means restricted to the aforementioned details which are described only as examples; they may vary within the framework of the invention, as defined in the following claims.

It will thus be seen that the objects set forth above, among those made apparent from the preceding description, are efficiently attained and, since certain changes may be made in the above constructions without departing from the spirit and scope of the invention, it is intended that all matter contained in the above description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

What is claimed is:

1. Apparatus for indicating the freezing of the surface of an asphalt road, paved runway, or the like, said apparatus comprising a detecting transmitter device installed in operative proximity with a surface to be observed, said detecting transmitter device including an ultrasonic waveguide installed on the surface to be observed; and electronic equipment electrically connected to the ultrasonic waveguide for transmitting ultrasonic waves to said ultrasonic waveguide, said ultrasonic waves proceeding in said waveguide, and receiving said ultrasonic waves from said waveguide, the degree of attenuation of said ultrasonic waves in said waveguide depending upon the difference in viscosity and other mechanical properties of water and ice, whereby said detecting transmitter device and said electronic equipment detect freezing of said surface by attenuation of said ultrasonic waves in said waveguide.

2. Apparatus as claimed in claim 1, wherein said ultrasonic waveguide is wire-shaped.

3. Apparatus as claimed in claim 1, wherein said ultrasonic waveguide is tape-shaped.

4. Apparatus as claimed in claim 1, wherein said electronic equipment includes a transmitter device comprising a bar at least partially of magnetostrictive material and an electromagnetic winding around the bar for producing and detecting said ultrasonic waves.

5. Apparatus as claimed in claim 1, wherein said ultrasonic wave vibrates in said waveguide at a frequency in the range of 100 to 150 kHz.

6. Apparatus as claimed in claim 5, wherein said waveguide comprises metal having a maximum cross-sectional dimension less than approximately one tenth the wavelength of the ultrasonic vibration.

7. Apparatus as claimed in claim 1, wherein said waveguide comprises a wire having a substantially circular cross-section with a diameter of approximately 2 mm and of sufficiently high mechanical resistance.

8. Apparatus as claimed in claim 1, wherein said waveguide comprises a metal tape having a substantially rectangular cross-section with a larger dimension of approximately 6 mm and a smaller dimension of approximately 2 mm and of sufficiently high mechanical resistance.

9. Apparatus as claimed in claim 1, wherein said waveguide has a surface and a vertical dimension and said surface has a groove with a depth substantially equal to the vertical dimension of said waveguide, said groove having walls, said waveguide being positioned in said groove and said groove remaining open to insure access of water and ice between the walls of said groove and the surface of said waveguide.

* * * * *